United States Patent [19]

Gries et al.

[11] Patent Number: 5,766,616
[45] Date of Patent: Jun. 16, 1998

[54] METHOD AND COMPOSITION OF CHEMICALS FOR ATTRACTING AND CONTROLLING THE DOUGLAS-FIR TUSSOCK MOTH

[75] Inventors: Gerhard Gries, Coquitlam.; Keith N. Slessor, Maple Ridge; Regine Gries, Coquitlam; Grigori Khaskin, Port Moody; Priyantha D. C. Wimalaratne, Burnaby; Gary Grant, Sault Ste. Marie, all of Canada

[73] Assignee: Simon Fraser University, Burnaby, Canada

[21] Appl. No.: 509,573

[22] Filed: Jul. 31, 1995

[51] Int. Cl.$^6$ ............ A01M 49/00; A01M 5/02; A01M 5/06
[52] U.S. Cl. ............................ 424/405; 424/84
[58] Field of Search ......................... 424/84, 405

[56] References Cited

U.S. PATENT DOCUMENTS

| | | | |
|---|---|---|---|
| 3,485,868 | 12/1969 | Eddy et al. | 424/84 |
| 4,170,631 | 10/1979 | Young et al. | 424/19 |
| 4,216,202 | 8/1980 | Klun et al. | 424/84 |
| 4,324,931 | 4/1982 | Ishihara et al. | 570/189 |
| 4,563,348 | 1/1986 | Soderstrom et al. | 424/84 |
| 4,774,084 | 9/1988 | Magnusson et al. | 424/84 |
| 5,133,150 | 7/1992 | Briese | 43/122 |
| 5,236,715 | 8/1993 | McDonough et al. | 424/84 |

OTHER PUBLICATIONS

Smith et al; J. Org. Chem., 43(12), 2361–65(1978) Bestman et al., Tetrahedron Letters, 26(50), 6171–74(85) L.L. Sower, CRC, vol II, 166–73.

*Primary Examiner*—Thurman K. Page
*Assistant Examiner*—Murthy Sikha
*Attorney, Agent, or Firm*—Oyen Wiggs Green & Mutala

[57] ABSTRACT

This invention relates to novel methods and compositions for attracting and controlling the Douglas-fir tussock moth (DFTM). More specifically, this invention pertains to the use of novel pheromone combinations and methods to attract and control DFTM which is a major defoliator of Douglas-fir and other true firs. A composition for manipulating the behaviour of Douglas-fir tussock moths comprising: (a) Z6-heneicosen-11-one (Z6); and (b) one or more compounds from the group consisting of: (Z)6,(E)8-heneicosadien-11-one; (Z)6, (E) 9-heneicosadien-11-one; and (Z)6,(Z)9-heneicosadien-11-one.

11 Claims, 6 Drawing Sheets

METHOD AND COMPOSITION OF CHEMICALS FOR ATTRACTING AND CONTROLLING THE DOUGLAS-FIR TUSSOCK MOTH

FIELD OF THE INVENTION

This invention relates to novel methods and compositions for attracting and controlling the Douglas-fir tussock moth (DFTM). More specifically, this invention pertains to the use of novel pheromone combinations and methods to attract and control DFTM which is a major defoliator of Douglas-fir and other true firs.

BACKGROUND OF THE INVENTION

The Douglas-fir tussock moth (DFTM) is one of the most important defoliators of Douglas-fir and true firs in western North America (1). For example, when in 1974, 279,000 hectares of forest were defoliated, the Environmental Protection Agency provided an emergency exemption (2) that allowed application of the banned insecticide DDT to 161,000 hectares to contain the outbreak. Aerial applications of nucleopolyhedrosis virus and *Bacillus thuringiensis* offer alternatives for DFTM control (3). Following the discovery of the sex pheromone component (Z)6-heneicosen-11-one (Z6) (4), synthetic Z6 has been used in traps to detect and monitor DFTM infestations (5). However, Z6 unspecifically attracts 7 species of tussock moths, including white marked tussock moth (WMTM), *O. leucostigma*, rusty tussock moth, *O. antiqua* and western tussock moth, *O. cana* (6). Moreover, Z6 is less attractive than DFTM females, supporting the contention that female DFTM produce an additional sex pheromone component (6).

Sex pheromone blends have been discovered in many moths (7), and for several species syntheses of pheromone components or their use to monitor and/or control the target insects have been patented (8).

SUMMARY OF THE INVENTION

Three candidate pheromone components, (Z)6, (Z)9-, (Z)6, (E)8- and (Z)6, (E)9-heneicosadien-11-one [Z6Z9, Z6E8,Z6E9] have been identified in sex pheromone gland extracts of female Douglas-fir tussock moths (DFTM), *Orgyia pseudotsugata*. In field experiments, Z6E8 in combination with (Z)6-heneicosen-11-one (Z6) has been discovered to be highly attractive. Attractiveness of the blend of Z6 plus Z6E8 was discovered to exceed that of either component alone ten to twenty times. The essence of the invention is the preparation and use of Z6 plus Z6E8 for monitoring and control of DFTM populations.

The invention is directed to a composition for manipulating the behaviour of Douglas-fir tussock moths comprising: (a) Z6-heneicosen-11-one; and (b) a compound selected from the group consisting of: (Z)6, (E)8-heneicosadien-11-one; (Z)6, (E)9-heneicosadien-11-one; and (Z)6, (Z)9-heneicosadien-11-one.

The composition in another embodiment can comprise (Z)6-heneicosen-11-one and a ketone which can rearrange, fully or in part, to (Z)6, (E)8-heneicosadien-11-one. In another variation, the composition can comprise (Z)6-heneicosen-11-one and (Z)6, (E)8-heneicosadien-11-one alone. The composition in a further form can comprise (Z)6-heneicosen-11-one, and two or more ketones which can rearrange, fully or in part, to (Z)6, (E)8-heneicosadien-11-one.

The composition in various forms can be contained in and released from a trap which captures attracted DFTM males.

Chemicals in the composition can be contained in and released from slow release devices.

The invention is also directed to the novel compound, synthetic (Z)6, (E)8-heneicosadien-11-one.

In a further embodiment, the invention is directed to a method of capturing Douglas-fir tussock moths which comprises baiting a trap with (a) Z6-heneicosen-11-one; and (b) a compound selected from the group consisting of: (Z)6, (E)8-heneicosadien-11-one; (Z)6, (E)9-heneicosadien-11-one; and (Z)6, (Z)9-heneicosadien-11-one.

In the method, the (a) Z6-heneicosen-11-one; and (b) compound selected from the group consisting of: (Z)6, (E)8-heneicosadien-11-one; (Z)6, (E)9-heneicosadien-11-one; and (Z)6, (Z)9-heneicosadien-11-one can be held in a slow release device.

In practising the method of the invention, the (a) Z6-heneicosen-11-one; and (b) compound selected from the group consisting of: (Z)6, (E)8-heneicosadien-11-one; (Z)6, (E)9-heneicosadien-11-one; and (Z)6, (Z)9-heneicosadien-11-one can be held in a trap which captures attracted DFTM males. The composition in its simplest form can comprise (Z)6-heneicosen-11-one and (Z)6, (Z)8-heneicosadien-11-one.

BRIEF DESCRIPTION OF THE DRAWINGS

In drawings which illustrate specific embodiments of the invention, but which should not be construed as restricting the spirit or scope of the invention in any way.

DETAILED DESCRIPTION OF THE PREFERRED EMBODIMENT

Analysis of Sex Pheromone Gland Extracts

Three candidate pheromone components, (Z)6, (Z)9-, (Z)6, (E)8- and (Z)6, (E)9-heneicosadien-11-one [Z6Z9, Z6E8, Z6E9] were identified in sex pheromone gland extracts of female Douglas-fir tussock moths (DFTM), *Orgyia pseudotsugata*.

Pheromone extract analyses of laboratory-reared white marked tussock moths (WMTM), by coupled gas chromatographic-electroantennographic detection GC-EAD (10, 16) revealed antennal responses to Z6 and to several unknown components, one of which gave coupled gas chromatographicmass spectrometric GC-MS (11) parent and fragmentation ions indicative of a diunsaturated ketone. Because a diene ketone, 1,Z6-heneicosadien-11-one, had previously been identified in DFTM pheromone extract (12), and considering that Z6,Z9-dienepoxides are common pheromones in geometrid and arctiid moths (7), we synthesized Z6,Z9-heneicosadien-11-one (Z6Z9) (see FIGS. 1 and 2).

Figure 1:
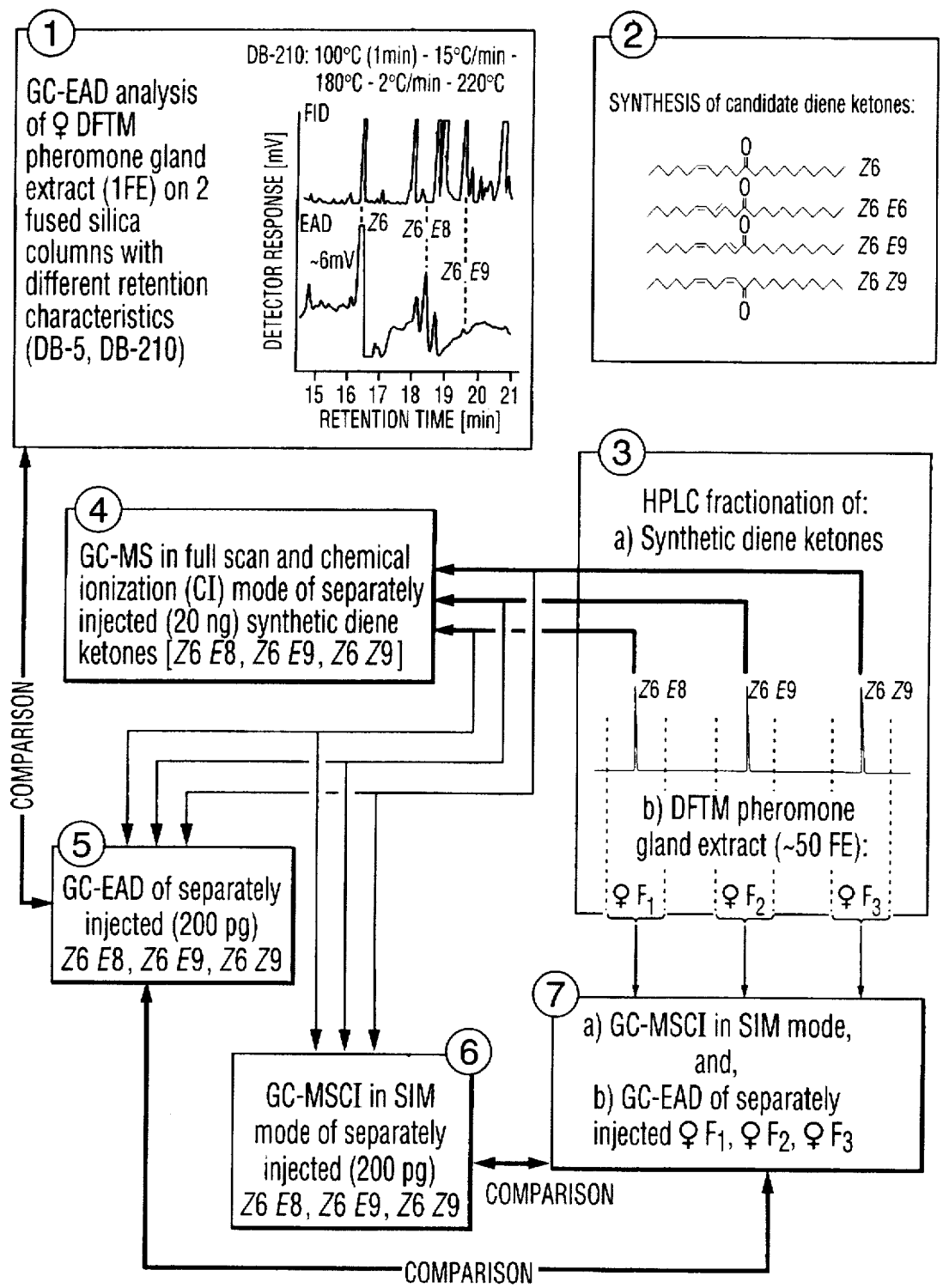
FIG. 1 illustrates schematically the procedure for the identification of (Z6), (E8)-, (Z)6, (E)9, and (Z)6, (Z)9-heneicosadien-11-one (Z6E8, Z6E9, Z6Z9) in female Douglas-fir tussock moth (DFTM) pheromone gland extract.

FIG. 1 illustrates schematically the procedure for the identification of (Z6), (E8)-, (Z)6, (E)9 and (Z)6, (Z)9-heneicosadien-11-one (Z6E8, Z6E9, Z6Z9) in female Douglas-fir tussock moth (DFTM) pheromone gland extract. FE=female equivalent of pheromone extract; Female F1=fraction 1 of female DFTM pheromone gland extract; GC-EAD=gas chromatographic-electroantennographic detection (10); HPLC=high performance liquid chromatography (18); GC-MSCI=gas chromatrographic-mass spectrometric analyses in chemical ionization mode (20); SIM= selected ion monitoring mode.

Synthetic Z6Z9 in solution at room temperature and during GC-analyses rearranged to Z6E8, Z6E9 and other dienones, as determined by nuclear magnetic resonance NMR spectroscopy (13) and syntheses (14) of identified rearrangement products. Identical GC retention times of Z6Z9 and Z6E8 indicated conversion of Z6Z9 to Z6E8, analogous to the deconjugations reported for α, β-unsaturated ketones (15).

Figure 1A:
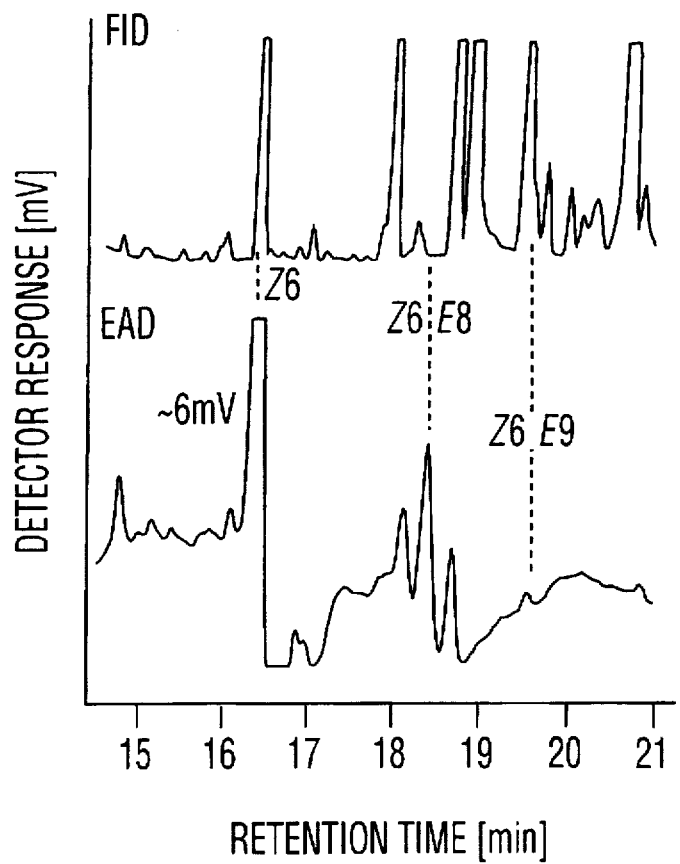
FIG. 1a illustrates flame ionization detector (FID) and electroantennographic detector (EAD: male DFTM antenna) responses to 1 female equivalent of female DFTM pheromone gland extract. Chromatography: splitless injection; injector and detector temperature 240° C.; DB-210 column; 100° C. (1 min.), 15° C./min. to 180° C., 2° C./min. to 220° C.
Figure 1B:
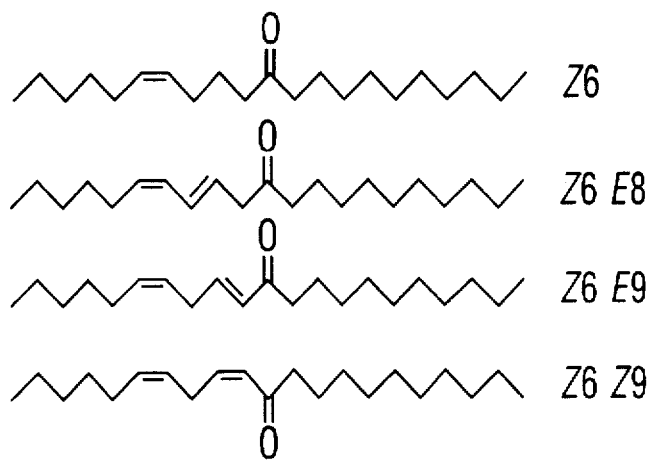
FIG. 1b illustrates graphically compounds identified in pheromone gland extracts of female DFTM. Chemical abbreviations as in FIG. 1.
Figure 1C:
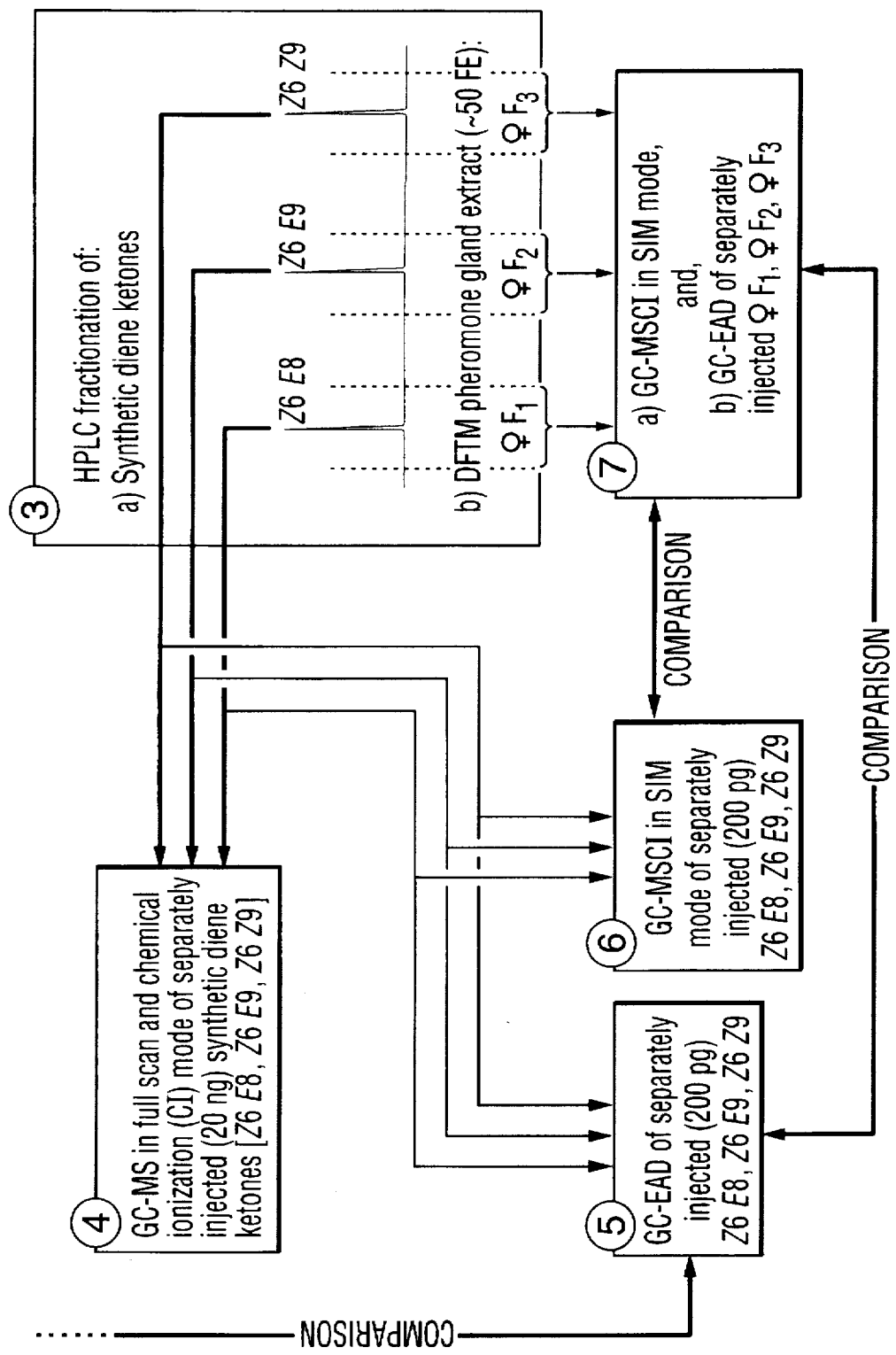
FIG. 1c illustrates sequentially the analytical procedures followed to identify diene ketones in pheromone gland extracts of female DFTM. Abbreviations as in FIG. 1.

GC-EAD analyses of DFTM pheromone extract (16) revealed several compounds consistently eliciting responses from male DFTM antennae, with Z6 being most abundant and most EAD-active (see FIG. 1a which illustrates flame ionization detector (FID) and electroantennographic detector (EAD: male DFTM antenna) responses to 1 female equivalent of female DFTM pheromone gland extract, Chromatography: splitless injection; injector and detector temperature 240° C.; DB-210 column; 100° C. (1 min.), 15° C./min. to 180° C., 2° C./min. to 220° C.). Comparative GC-EAD analysis (17) of pheromone extract and synthetic dienones resulted in retention time matches of two EAD-active female-produced compounds with synthetic Z6E8 and Z6E9.

With known high performance liquid chromatography HPLC (18) retention times of synthetic Z6E8, Z6E9 and Z6Z9(19), the corresponding fractions of DFTM pheromone gland extract were isolated (see FIG. 1; 3a,b). Each synthetic dienone was then analyzed by GC-MS (11) in full scan and CI mode to determine diagnostic ions for SIM (FIG. 1; 4), which provided highly increased sensitivity. GC-MSCI-SIM of synthetic dienones and corresponding DFTM extract fractions (see FIG. 1; 6,7a) resulted in good retention time and ion ratio matches between synthetic and female-produced Z6E8 and Z6E9.

During GC-MSCI-SIM, HPLC-fractionated synthetic Z6Z9 and DFTM-dienone in the corresponding HPLC extract fraction (see FIG. 1;3) rearranged to compounds with identical retention and ion ratio characteristics, thereby confirming the presence of Z6Z9 in the DFTM pheromone extract. Moreover, comparative GC-EAD of synthetic dienones (FIG. 1; 5) and corresponding DFTM extract fractions (FIG. 1; 7b) revealed comparable antennal response patterns.

Attraction of Douglas-fir Tussock Moth Males to Synthetic Test Chemicals

Example 1

A 4-treatment, 12-replicate experiment was conducted in a mature Douglas fir stand west of Kamloops, British Columbia, Canada. Unitraps (21) were suspended 1.5 m above ground from trees in randomized complete blocks with traps and blocks at 25 m intervals. During peak flight activity of DFTM males just prior to dusk, HPLC-purified dienones in acetonitrile were carried on dry ice to the Unitraps (21), and were syringed onto small cotton wicks (22) affixed to trap lids.

Recording the number of trap-captured DFTM males 40 minutes later, Z6 alone, and in combination with Z6E9 had not attracted any males (see FIG. 2).

Figure 2:
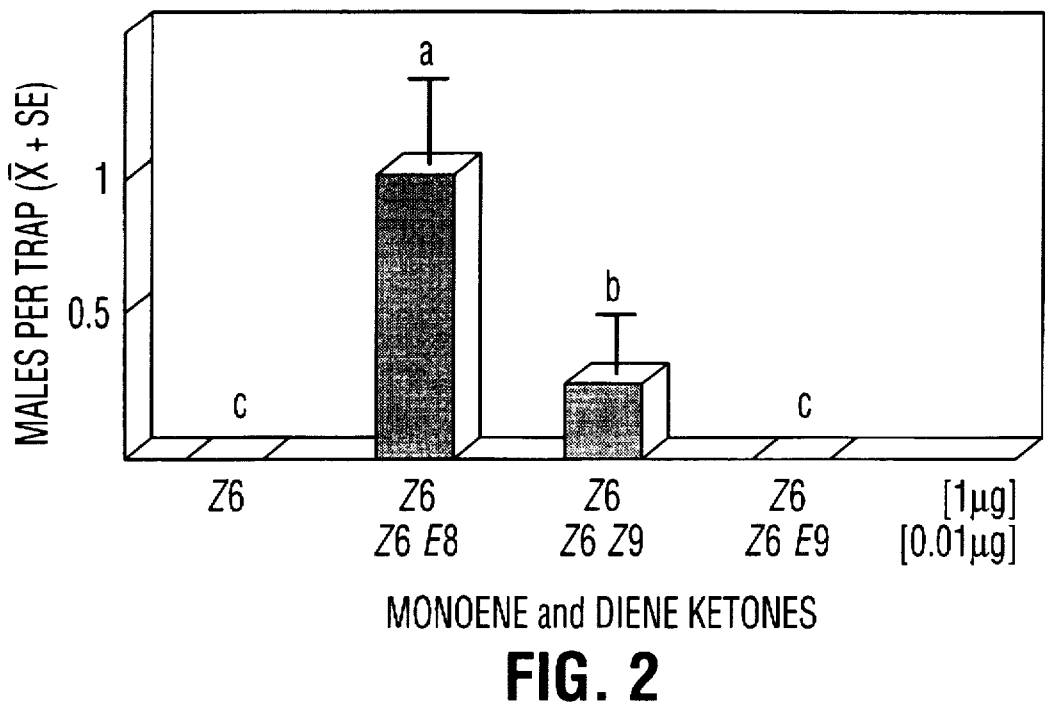
FIG. 2 illustrates by three dimensional bar graphs, the capture of male Douglas-fir tussock moths during a 40 min. experiment in Unitraps.

FIG. 2 illustrates by three dimensional bar graph, the capture of Douglas fir tussock moth males during a 40 min. experiment in Unitraps (21) baited with rubber septa impregnated with (Z)6-heneicosen-11-one (Z6) alone and in combination with either (Z)6, (E)8-, (Z)6, (E)9- or (Z)6, (Z)9-heneicosadien-11-one [Z6E8, Z6E9, Z6Z9]. Kamloops, British Columbia, Canada, 7 September, 6:30 to 7:10 p.m., 1993; N=12. Bars superscripted by a different letter are significantly different [non-parametric analysis of variance by ranks (Friedman's test) followed by comparison of means (Bonferroni (Dunn) T. test) (24) P<0.05].

Attraction of males to Z6E8 in combination with Z6 (FIG. 2) indicated, however, that this dienone is a potent sex pheromone component in DFTM. The apparent attractiveness of Z6Z9 in combination with Z6 can be attributed to partial rearrangement of Z6Z9 to Z6E8 during the 40 min. test.

Example 2

Extensive 1994 field tests in Vinsulla, British Columbia, substantiated the superior attractiveness of the two-component pheromone blend [Z6 plus Z6E8]. Attractiveness of this blend exceeded that of either component alone by ten to twenty times.

Figure 3:
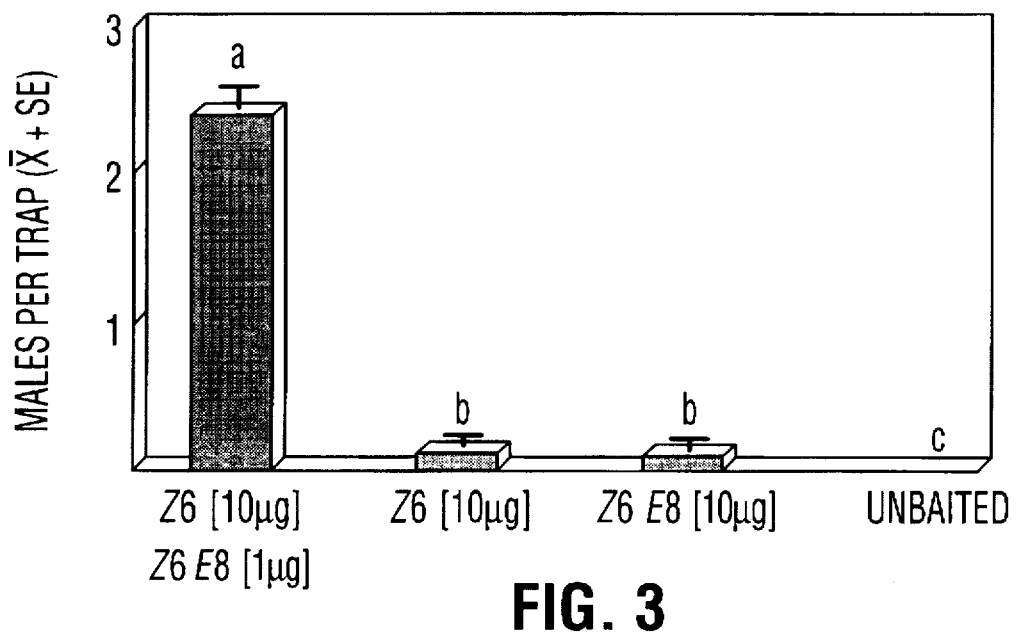
FIG. 3 illustrates by three dimensional bar graphs the captures of Douglas-fir tussock moth males in 2-liter-delta-milk-carton traps (21) baited with cotton wicks (22) that were impregnated with (Z)6-heneicosen-11-one (Z6), (Z)6, (E)8-heneicosadien-11-one (Z6E8) or both combined.

FIG. 3 illustrates by three dimensional bar graphs captures of Douglas-fir tussock moth males in 2-liter-delta-milk-carton traps (21) baited with cotton wicks (22) that were impregnated with (Z)6-heneicosen-11-one (Z6), (Z)6, (E)8-heneicosadien-11-one (Z6E8) or both combined. Vinsulla, British Columbia, 2:00–6:45 p.m., Sep. 17, 1994; 10 replicates. Bars superscripted by the same letter are not significantly different [non-parametric analysis of variance by ranks (Friedman's test) followed by comparison of means (Bonferroni (Dunn) T test) (24), P<0.05].

Example 3

Figure 4:
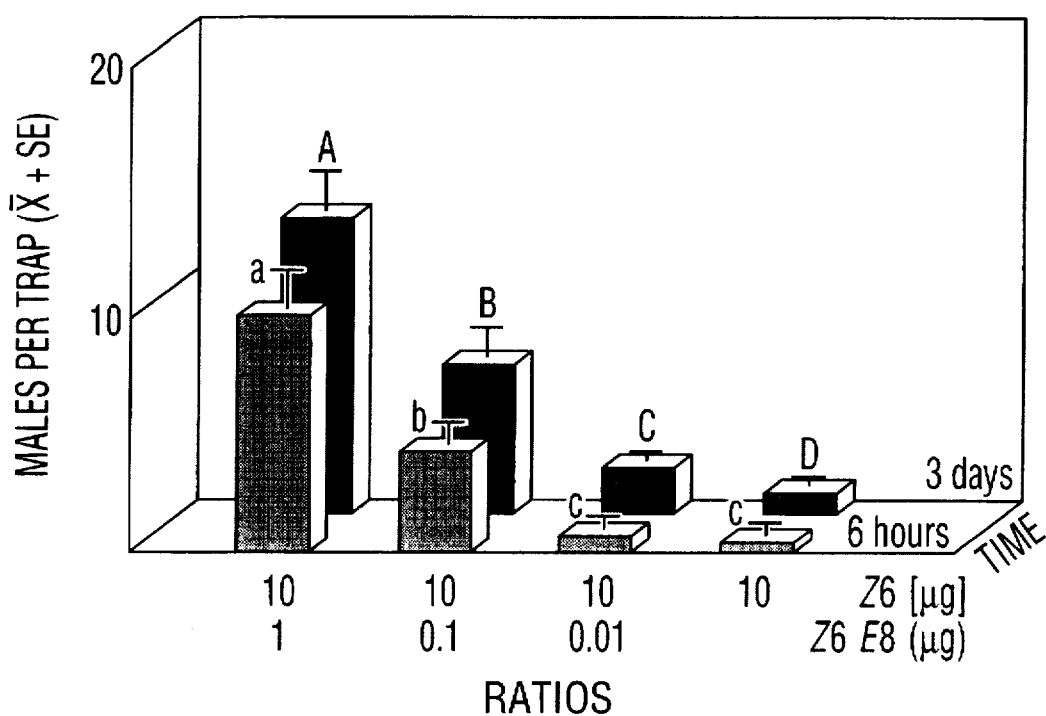
FIG. 4 illustrates by three dimensional bar graphs captures of Douglas-fir tussock moth males in 2-liter-delta-milk-carton traps (21) baited with cotton wicks (22) that were impregnated with (Z)6-heneicosen-11-one (Z6) alone and in combination with (Z)6, (E)8-heneicosadien-11-one (Z6E8) at increasing proportions.

In a ratio experiment, attraction of DFTM males to Z6 increased with increasing proportions of Z6E8. FIG. 4 illustrates by three dimensional bar graphs the captures of Douglas-fir tussock moth males in 2-liter-delta-milk-carton traps (21) baited with cotton wicks (22) that were impregnated with (Z)6-heneicosen-11-one (Z6) alone and in combination with (Z)6, (E)8-heneicosadien-11-one (Z6E8) at increasing proportions. Lures were not changed between trapping periods. Vinsulla, British Columbia, Sep. 10–13, 1994; 10 replicates. For each trapping period, bars superscripted by the same letter are not significantly different [non-parametric analysis of variance by ranks (Friedman's test) followed by comparison of means (Bonferroni (Dunn) T test (24), P<0.05].

Example 4

Figure 5:
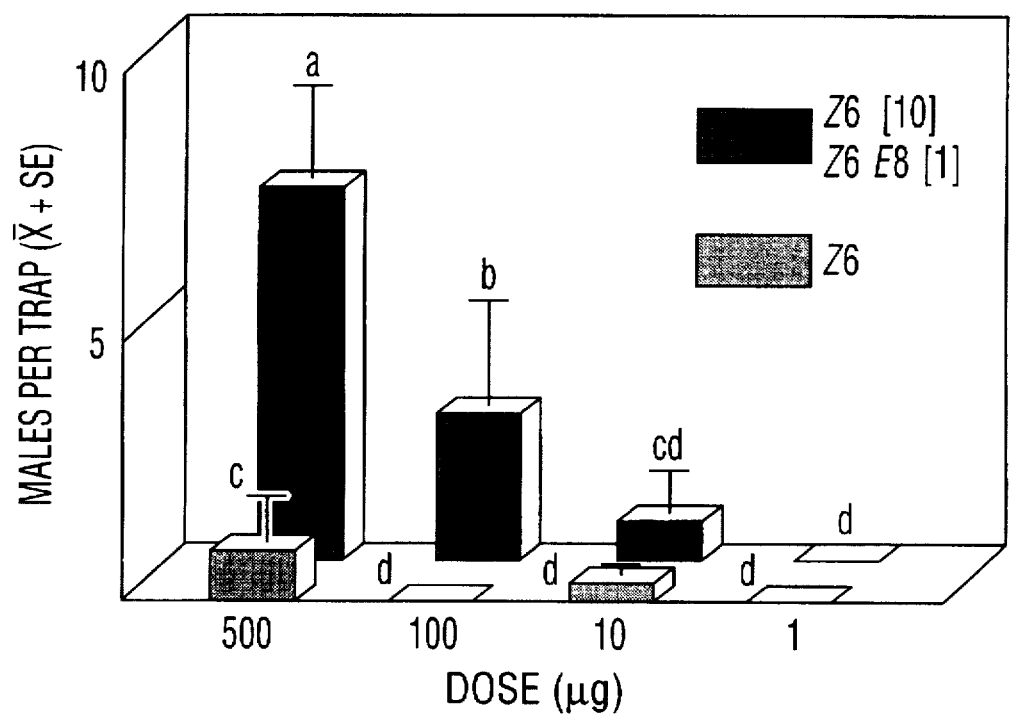
FIG. 5 illustrates by three dimensional bar graphs captures of Douglas-fir tussock moth males DFTM in 2-liter-delta-milk-carton traps (21) baited with cotton wicks (22) that were impregnated with (Z)6-heneicosen-11-one (Z6) alone or in combination with (Z)6, (E)8-heneicosadien-11-one (Z6E8) at increasing doses.

In a dose-response experiment with increasing doses of Z6E8, 10 ug of the 2-component blend were as attractive as 500 ug of Z6 by itself. FIG. 5 illustrates by three dimensional bar graphs captures of Douglas-fir tussock moth males in 2-liter-delta-milk-carton traps (21) baited with cotton wicks (22) that were impregnated with (Z)6, (E)8-heneicosadien-11-one at increasing doses. Vinsulla, British Columbia, Sep. 17–24, 1994; 5 replicates. Bars superscripted by the same letter are not significantly different [non-parametric analysis of variance by ranks (Friedman's test) followed by comparison of means (Student Newman Keuls test) (24), P<0.05].

Example 5

Figure 6:
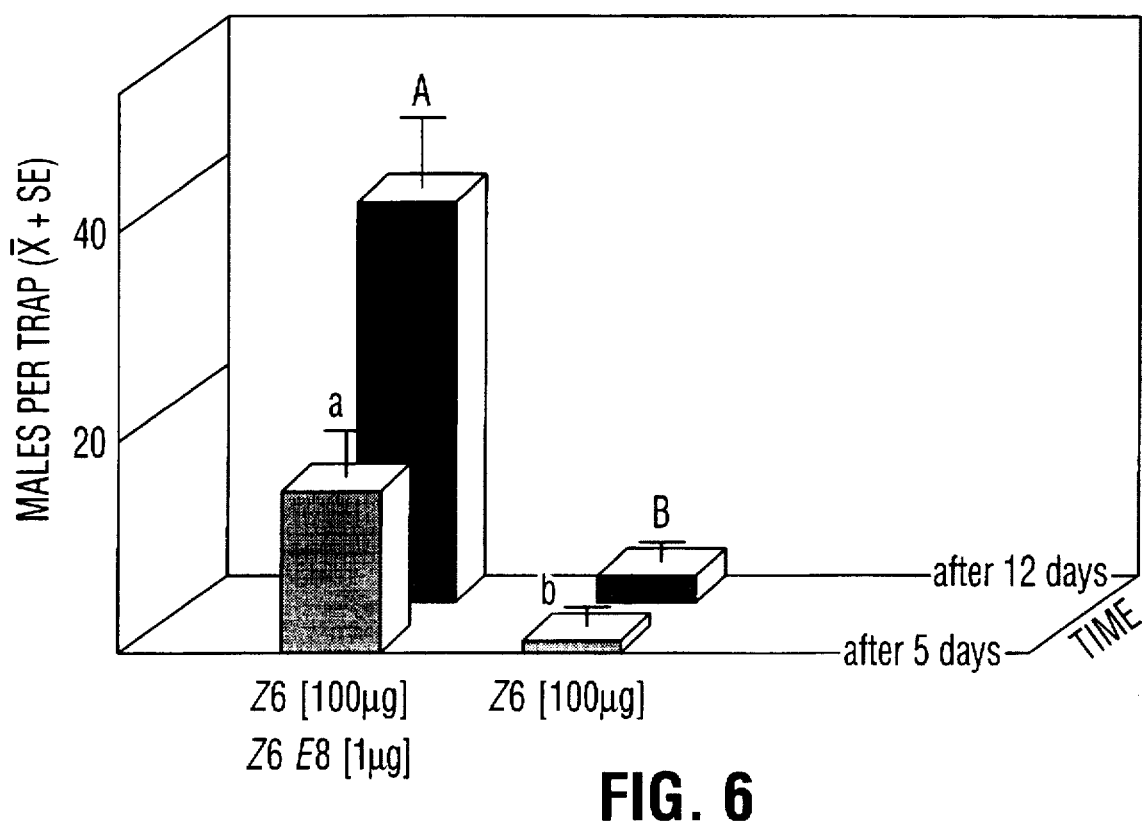
FIG. 6 illustrates by three dimensional bar graphs captures of Douglas-fir tussock moth males in Unitraps (21) baited with rubber septa (22) that were impregnated with (Z)6-heneicosen-11-one (Z6) alone or in combination with (Z)6, (E)8-heneicosadien-11-one (Z6E8).

Superior attractiveness of Z6 plus Z6E8 versus Z6 alone was also confirmed when chemicals were released from rubber septa instead of cotton. FIG. 6 illustrates by three dimensional bar graphs capture of Dougas-fir tussock moth males in Unitraps (21) baited with rubber septa (22) that were impregnated with (Z)6-heneicosen-11-one (Z6) alone or in combination with (Z)6, (E)8-heneicosadien-11-one (Z6E8). Vinsulla, British Columbia, Sep. 5–17, 1994; 12 replicates. Lures were not changed after 5 days. For each trapping period, treatments were significantly different [non-parametric Wilcoxon test (24), p<0.05].

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

APPENDIX

1. B. E. Wickman, U.S. Dept. Agric. Tech. Bull. 1585 (1978); R. R. Mason and B. E. Wickman, in A. A. Berryman (ed.), Dynamics of forest insect populations. Plenum, New York (1988).

2. Environmental Protection Agency, Federal Register 39, No. 44, pp. 8377–8381 (1974).

3. M. J. Stelzer, J. Neisess, C. G. Thompson, J. Econ. Entomol. 68: 269 (1975).

4. R. G. Smith, G. E. Daterman, G. D. Daves, Jr., Science 188: 63 (1975).

5. G. E. Daterman, in M. H. Brooks, R. W. Stark, and R. W. Campbell (eds.), The Douglas-fir tussock moth: a synthesis. U.S. Forest Service Tech. Bull. 1585 (1878); G. E. Daterman, R. L. Livingston, J. M. Wenz, L. L. Sower, USDA Douglas-fir tussock moth handbook (1979); G. E. Daterman, in A. A. Berryman and L. Safranyik (eds.), Dispersal of forest insects: evaluation, theory and management implications. Proceedings of second IUFRO conf. (1980); G. E. Daterman, in A. F. Kydonieus and M. Beroza (eds.), Insect suppression with controlled release pheromone systems. CRC Press Inc., Boca Raton, Fla. (1982); R. F. Shepherd, T. G. Gray, R. J. Chorney, G. E. Daterman, Can. Entomol. 117, 839 (1985).

6. G. E. Daterman, C. J. Peterson, R. G. Robbins, L. L. Sower, G. D. Daves, Jr., R. G. Smith, Environ. Entomol. 5, 1187 (1976); Grant, G. G., Environ. Entomol. 6: 739 (1977).

7. H. Arn, M. Tóth, E. Priesner, List of sex pheromones of Lepidoptera and related attractants. International organization for biological control. 2nd ed. (1992).

8. For instance: L. M. McDonough, H. G. Davis, Sex attractant for the mint root borer. U.S. Pat. No. 5,236,715 (1933); Schwarz, Meyer, Klun, J. A. Snow, J. Wendell, Octadienyl acetate synergist for the grape root borer pheromone. U.S. Pat. No. 4,931,032 (1990); R. T. Carde, J. P. Kochansky, W. L. Roelofs, Sex pheromone for potato tubeworm moth, *Phthorimea operculella*. U.S. Pat. No. 4,010, 255 (1977); R. J. Anderson, C. A. Henrick, synthesis of the pink bollworm sex pheromone. U.S. Pat. No. 3,919,329 (1975).

9. H. Arn, E. Städler, S. Rauscher, Z. Naturforsch. 30c, 722 (1975).

10. Gas chromatographic-electroantennographic detection (GC-EAD) analyses were carried out using a Hewlett Packard 5890A gas chromatograph equipped with a fused silica column (30 m×0.25 mm ID) coated with either DB-210 or DB-5 (J&W Scientific, Folsom, Calif. 95630).

11. Hewlett Packard 5985B GC-mass spectrometer equipped with a DB-210 column (10).

12. L. M. Smith, R. G. Smith, T. M. Loehr, G. D. Daves, Jr., G. E. Daterman, R. H. Wohleb, J. Org. Chem. 43, 2361 (1978).

13. $^1$H two-dimensional and nuclear Overhauser magnetic resonance (NMR) spectroscopy was carried out on a Bruker AMX-400 spectrometer at 400.13 and 100.62 MHz for $^{13}$C.

14. A detailed description of synthetic procedures and complete characterizations of all dienones will be given elsewhere.

15. R. Ricard, P. Sauvage, C. S. K. Wan, A. C. Weedon, D. F. Wong, J. Org. Chem. 51, 62 (1986).

16. DFTM male and female pupae were collected around Kamloops, B.C., and kept separately in filter paper-lined Petri dishes at 24° C. and a 14L: (10)D photoperiod. At the onset of the scotophase [G. G. Grant, D. Frech, D. Grisdale, Ann. Entomol. Soc. America 68, 519 (1975)], pheromone glands of 2 day-old virgin females were removed and extracted for 5 min in hexane. Aliquots of 1 female equivalent of gland extracts were analyzed by GC-EAD (10).

17. These GC-EAD analyses employed fused silica columns coated with DB-210 or DB-5 (10).

18. High performance liquid chromatography (HPLC) employed a Waters LC 625 high performance liquid chromatograph equipped with a Waters 486 variable wavelength UV-visible detector system set at 220 nm, a HP 3396 series II integrator, and a Nova-Pak TM C18 (3.9×300 mm) column. Flow rate of acetonitrile was 1 ml/min.

19. During HPLC unlike GC analyses (synthetic) Z6Z9does not rearrange.

20. Retention time and ion ratio matches of synthetic versus female-produced dienones [GC-MSCI-SIM, retention time, m/z (relative intensity)]: synthetic Z6Z8: 18.6 min. 307 (100), 308 (23.9), DFTM gland extract: 18.6 min.

307 (100), 308 (25.6); synthetic Z6E9: 19.7 min, 307 (100), 308 (22.9), DFTM gland extract, 19.7 min, 307 (100), 308 (33.2); synthetic Z6Z9; 18.6 min, 307 (100), 308 (26.7), DFTM gland extract, 18.6 min, 307 (100), 308 (20.7).

21. Trap designs: a) Green Unitraps (Phero Tech Inc., Delta, B.C.); a small Dichlorvos cube (Green Cross, division of Ciba, Geigy Canada Ltd., Mississauga, ON) placed on the bottom of traps assured rapid killing of captured moths; b) 2-liter-Delta-milk-cartons: the inner 855 $cm^2$ surface was covered with adhesive Tangle-Trap (Tanglefoot Company, Grand Rapids Mich.) to retain moths approaching the chemical lure in the middle of the trap.

22. Release devices: a) gray sleeve stoppers (West, Company, Phoenixville, Pa.), and b) cotton wicks ($\phi$⅛") (Richmond Dental Company™, Charlotte, N.C.) cut to 1 cm length.

23. (Z)6-heneicosen-11-one was >98% chemically pure and was purchased from Phero Tech Inc., Delta, British Columbia, Canada V4G 1E9.

24. SAS/STAT User's guide, 1988, release 6.03 edition, SAS Institute Inc., Cary, N.C., 27513.

What is claimed is:

1. A composition for manipulating the behaviour of Douglas-fir tussock moths comprising:
   (a) Z6-heneicosen-11-one; and
   (b) a compound selected from the group consisting of:
      (Z)6, (E)8-heneicosadien-11-one,
      (Z)6, (E)9-heneicosadien-11-one, and
      (Z)6, (Z)9-heneicosadien-11-one.

2. A composition as claimed in claim 1 comprising (Z)6-heneicosen-11-one and a ketone which rearranges, fully or in part, to (Z)6, (E)8-heneicosadien-11-one.

3. A composition as claimed in claim 1 comprising (Z)6-heneicosen-11-one and (Z)6, (E) 8-heneicosadien-11-one.

4. A composition as claimed in claim 1 comprising (Z)6-heneicosen-11-one, and two or more ketones which rearrange, fully or in part, to (Z)6, (E) 8-heneicosadien-11-one.

5. A composition as claimed in claim 1 wherein the composition is contained in and released from a trap which captures attracted DFTM males.

6. A composition as claimed in claim 1 wherein chemicals in the composition are contained in and released from slow release devices.

7. A method of capturing Douglas-fir tussock moths which comprises baiting a trap with
   (a) Z6-heneicosen-11-one; and
   (b) a compound selected from the group consisting of:
      (Z)6, (E)8-heneicosadien-11-one,
      (Z)6, (E)9-heneicosadien-11-one, and
      (Z)6, (Z)9-heneicosadien-11-one.

8. A method as claimed in claim 7 wherein the
   (a) Z6-heneicosen-11-one; and
   (b) a compound selected from the group consisting of:
      (Z)6, (E)8-heneicosadien-11-one,
      (Z)6, (E)9-heneicosadien-11-one, and
      (Z)6, (Z)9-heneicosadien-11-one are held in a slow release device.

9. A method as claimed in claim 7 wherein the
   (a) Z6-heneicosen-11-one; and
   (b) a compound selected from the group consisting of:
      (Z)6, (E)8-heneicosadien-11-one,
      (Z)6, (E)9-heneicosadien-11-one, and
      (Z)6, (Z)9-heneicosadien-11-one are held in a trap which captures attracted DFTM males.

10. A method as claimed in claim 7 wherein the composition comprises (Z)6-heneicosen-11-one and (Z)6, (E)8-henecosadien-11-one.

11. A method as claimed in claim 7 wherein the composition comprises (Z)6-heneicosen-11-one and a ketone which rearranges, fully or in part, to (Z)6, (E)8-heneicosadien-11-one.

* * * * *